(12) United States Patent
Craine et al.

(10) Patent No.: US 8,684,923 B2
(45) Date of Patent: Apr. 1, 2014

(54) METHODS SYSTEMS, AND COMPUTER PROGRAM PRODUCTS FOR AGGREGATING MEDICAL INFORMATION

(75) Inventors: Ari Craine, Marietta, GA (US); Jonathan Reeves, Roswell, GA (US); Steven Tischer, Atlanta, GA (US)

(73) Assignee: AT&T Intellectual Property I, LP, Atlanta, GA (US)

( * ) Notice: Subject to any disclaimer, the term of this patent is extended or adjusted under 35 U.S.C. 154(b) by 1782 days.

(21) Appl. No.: 11/581,912

(22) Filed: Oct. 17, 2006

(65) Prior Publication Data

US 2008/0139890 A1 Jun. 12, 2008

(51) Int. Cl.
*A61B 5/00* (2006.01)
*G06F 19/00* (2011.01)

(52) U.S. Cl.
CPC .................................. *G06F 19/3493* (2013.01)
USPC .......................................................... 600/301

(58) Field of Classification Search
USPC ................................................. 600/300–301
See application file for complete search history.

(56) References Cited

U.S. PATENT DOCUMENTS

| | | | |
|---|---|---|---|
| 4,445,118 A | 4/1984 | Taylor et al. | |
| 5,418,538 A | 5/1995 | Lau | |
| 5,663,734 A | 9/1997 | Krasner | |
| 5,663,735 A | 9/1997 | Eshenback | |
| 5,663,761 A | 9/1997 | Fukui | |
| 6,433,735 B1 | 8/2002 | Bloebaum et al. | |
| 7,109,859 B2 | 9/2006 | Peeters | |
| 7,570,158 B2* | 8/2009 | Denny et al. | 340/521 |
| 7,705,723 B2* | 4/2010 | Kahn et al. | 340/521 |
| 2003/0011511 A1 | 1/2003 | King et al. | |
| 2003/0129578 A1* | 7/2003 | Mault | 435/4 |
| 2003/0163351 A1* | 8/2003 | Brown et al. | 705/2 |
| 2004/0078219 A1* | 4/2004 | Kaylor et al. | 705/2 |
| 2004/0119591 A1* | 6/2004 | Peeters | 340/539.26 |
| 2004/0128161 A1* | 7/2004 | Mazar et al. | 705/2 |
| 2004/0178913 A1* | 9/2004 | Penuela et al. | 340/573.1 |
| 2004/0259494 A1* | 12/2004 | Mazar | 455/1 |
| 2005/0101841 A9* | 5/2005 | Kaylor et al. | 600/300 |
| 2006/0106433 A1* | 5/2006 | Mazar et al. | 607/60 |
| 2006/0206361 A1 | 9/2006 | Logan | |
| 2006/0290496 A1 | 12/2006 | Peeters | |
| 2009/0085873 A1* | 4/2009 | Betts et al. | 345/169 |
| 2011/0105856 A1* | 5/2011 | Haines et al. | 600/300 |
| 2011/0301437 A1* | 12/2011 | Gabriel et al. | 600/301 |

OTHER PUBLICATIONS

Gentag "An IP Development Company" 1 page (believed prior to Oct. 17, 2006) < http:www.gentag.com/ >.
Gentag "Gentag Technology—RFID Cell Phone Sensor Networks" 1-3 (believed prior to Oct. 17, 2006) < http://www.gentag.com/technology.xml >.

(Continued)

*Primary Examiner* — Bill Thomson
*Assistant Examiner* — Bobby Soriano
(74) *Attorney, Agent, or Firm* — Andrew Gust; Guntin & Gust, PLC

(57) ABSTRACT

A method of aggregating medical information can include receiving, at a remote aggregation system, individual syndromes collected by mobile personal medical devices associated with respective bodies as the mobile personal medical devices move within an environment, aggregating the individual syndromes at the remote aggregation system, and determining whether an environmental syndrome exists for at least some of the individual syndromes. Related systems and computer program products are also disclosed.

20 Claims, 11 Drawing Sheets

(56) References Cited

OTHER PUBLICATIONS

Gentag "Gentag Applications" 1-3 (believed prior to Oct. 17, 2006) < http://www.gentag.com/applications.xml >.

Gentag "Gentag Products" 1-2 (believed prior to Oct. 17, 2006) < http://www.gentag.com/products.xml >.

Gentag product description "Button Tag for (Pharma) Counterfeit Prevention" 1 page (believed prior to Oct. 17, 2006).

Gentag product description "Miniature RFID Hanger Tag" 1 page (believed prior to Oct. 17, 2006).

Gentag product description "RFID Laundry and Garment Tag" 1 page (believed prior to Oct. 17, 2006).

Gentag productdescription "RFID Smart Skin Patch for Identification and Diagnostics Applications" 1 page (believed prior to Oct. 17, 2006).

Gentag product description HF RFID Reader—Writer Multi-Protocol (Including NFC) 1 page (believed prior to Oct. 17, 2006).

Gentag "Gentag Team" 1-3 (believed prior to Oct. 17, 2006) < http://www.gentag.com/team.xml >.

Gentag "Gentag News" 1-2 (believed prior to Oct. 17, 2006) < http://www.gentag.com/news.xml >.

Gentag "Contact" (believed prior to Oct. 17, 2006) < http://www.gentag.com/contact.xml >.

* cited by examiner

METHODS SYSTEMS, AND COMPUTER PROGRAM PRODUCTS FOR AGGREGATING MEDICAL INFORMATION

CROSS-REFERENCE TO RELATED APPLICATIONS

This application is related to U.S. patent application Ser. No. 11/550,228 and Ser. No. 11/582,237, each filed concurrently with the present application, the entireties of which are incorporated herein by reference.

FIELD OF THE INVENTION

The present invention generally relates to the field of electronics in general, and more particularly, to methods devices and computer program products for mobile personal medical devices.

BACKGROUND

One of the problems faced by emergency medical providers, such as Emergency Medical Technicians (EMTs), is that a person in distress may not be able to communicate during an emergency. For example, a person may be experiencing a diabetic crisis, where the person is unable to answer questions asked by the EMTs.

Moreover, given the ease with which people are able to move throughout society and the world, it can be difficult to determine when an outbreak of a particular medical syndrome, such as Severe Acute Respiratory Syndrome (SARS) is underway. For example, a person may have contracted SARS before boarding an airplane to travel to another city, region or country. A SARS outbreak may, therefore, cross regional or international boundaries quite easily given the ease of travel. This mobility can make discovery of the syndrome difficult and, moreover, may place emergency medical providers in a somewhat reactive position so that the nature of the crisis is only understood after it is well underway.

In addition, legal restrictions on the handling of private medical information, such as the Health Insurance Portability And Accountability Act Of 1996 (HIPPA), require medical providers, such as doctors, EMTs, etc., to handle a person's private medical information as set out under the law. These legal restrictions may hinder the dissemination of critical medical information during a crisis which may place emergency medical providers at a further disadvantage during an outbreak.

SUMMARY

Embodiments according to the invention can provide methods, systems, and computer program products for aggregating medical information. Pursuant to these embodiments, a method of aggregating medical information can include receiving, at a remote aggregation system, individual syndromes collected by mobile personal medical devices associated with respective bodies as the mobile personal medical devices move within an environment, aggregating the individual syndromes at the remote aggregation system, and determining whether an environmental syndrome exists for at least some of the individual syndromes.

In some embodiments according to the invention, a system for aggregating medical information includes a processor circuit that is configured to receive individual syndromes collected by mobile personal medical devices associated with respective bodies as the mobile personal medical devices move within an environment and that is configured to aggregate the individual syndromes at the remote aggregation system and that is configured to determine whether an environmental syndrome exists for at least some of the individual syndromes.

Other systems, methods, and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

DESCRIPTION OF THE EMBODIMENTS ACCORDING TO THE INVENTION

Figure 1:
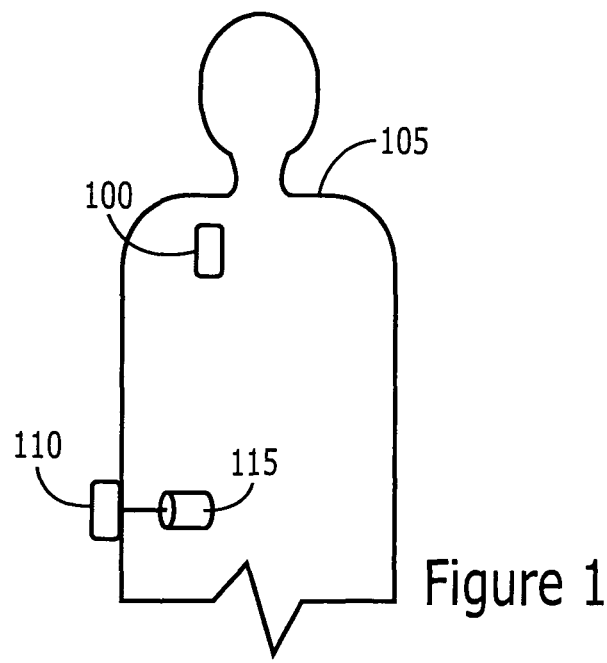
FIG. 1 is a schematic representation of a mobile personal medical device configured for in vivo implantation or coupling to in vivo implanted sensors according to some embodiments of the invention.

The present invention now is described more fully hereinafter with reference to the accompanying figures, in which embodiments of the invention are shown. This invention may, however, be embodied in many alternate forms and should not be construed as limited to the embodiments set forth herein. Like numbers refer to like elements throughout the description of the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

It will be understood that, when an element is referred to as being "coupled" to another element, it can be directly coupled to the other element or intervening elements may be present. In contrast, when an element is referred to as being "directly coupled" to another element, there are no intervening elements present.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense expressly so defined herein.

The present invention is described below with reference to diagrams (such as schematic illustrations) and/or operational illustrations of methods, devices, and computer program products according to embodiments of the invention. It is to be understood that the functions/acts noted in the figures may occur out of the order noted in the operational illustrations. For example, two elements shown in succession may in fact be executed substantially concurrently or the elements may sometimes be executed in the reverse order, depending upon the functionality/acts involved.

The present invention may be embodied in hardware and/or in software (including firmware, resident software, microcode, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

Computer program code or "code" for carrying out operations according to the present invention may be written in an object oriented programming language such as JAVA®, Smalltalk or C++, JavaScript, Visual Basic, TSQL, Perl, or in various other programming languages. Software embodiments of the present invention do not depend on implementation with a particular programming language. Portions of the code may execute entirely on one or more systems utilized by an intermediary server.

In some embodiments according to the invention, the computer program code may be provided to a processor circuit of a general purpose computer, special purpose computer, or other programmable data processing apparatus as instructions to produce a machine, such that the instructions, which execute via the processor circuit of the computer or other programmable data processing apparatus, create means for implementing the functions specified in the illustrations.

The computer code may be stored in a computer-readable memory that can direct a computer or other programmable data processing apparatus to function in a particular manner, such that the instructions stored in the computer-readable memory produce an article of manufacture including instruction means which implement the function specified in the illustrations.

As described herein below in greater detail, mobile personal medical devices can be configured for chronic in vivo implantation and can operate to receive and record parameters associated with functions of the body in which the device is implanted. For example, the mobile personal medical device can receive measurements regarding blood pressure, blood glucose level, blood oxygen, temperature, etc.

The measured parameters can be recorded and incorporated into previous measurements made over time to provide an ongoing record of the functions monitored by the mobile personal medical device. In some embodiments according to the invention, the mobile personal medical device can compare the measured parameters with known conditions or syndromes stored therein. If the measured parameters correlate to a syndrome stored in the mobile personal medical device, the device can transmit an alert signal or description of the syndrome as a warning.

In still other embodiments according to the invention, the mobile personal medical device can be configured to compare the measured parameters to known standards such as historical measurements of the individual body, regional, national, or international standards. Furthermore, the standards may be provided on the basis of an ethnic, racial, or cultural background. In operation, the mobile personal medical device can compare the measured parameters to the standards stored within the device and transmit an alert signal if any of the measured parameters (or any combination of the measured parameters) exceeds a threshold established for any of the standards.

Furthermore, the mobile personal medical device can transmit the alert after the threshold for the relevant parameter has been exceeded by a predetermined amount for a predetermined time. For example, the mobile personal medical device may not transmit the alert signal if the measured parameter exceeds the threshold only momentarily. In contrast, the mobile personal medical device may transmit the alert signal when the measured parameter exceeds the threshold for that parameter by either a relatively large amount or for a relatively long time.

In still other embodiments according to the invention, the mobile personal medical device can store geographic location information (such as that provided by a GPS circuit) to record the movements of the body in which the mobile personal medical device is implanted. Furthermore, the device may record proximity information regarding similar mobile personal medical devices that are detected. In particular, the device may record the detection of another nearby mobile personal medical device implanted in (or carried by) another person. This peer information may be useful in tracking communicable diseases.

In still further embodiments according to the invention, the mobile personal medical device is configured to communicate with remote systems, such as systems operated by authorized Emergency Medical Technicians (EMTs) or systems operated by medical providers, such as physicians. In such embodiments, the mobile personal medical device may upload and/or download information to/from the remote system. Accordingly, the mobile personal medical device may provide the record of measured parameters to the remote system for further analysis. Likewise, the remote system may download updated standards, and other data to the device for later operation. Furthermore, the remote system and the device may utilize a shared key to protect the privacy of the medical data stored therein. Accordingly, when the remote system requests access to information stored in the mobile personal medical device, the shared key may be used to authorize such access.

In still further embodiments according to the invention, the mobile personal medical device may be included as part of a wide scale aggregation system to monitor the medical situation for a local, regional, and/or national population. For example, the devices may be detectable by public sensors which can then relay information transmitted by the mobile personal medical devices to the aggregation system. The aggregation system can, in-turn, analyze the data forwarded by the mobile personal medical devices to determine whether similar syndromes or parameters are present in significant numbers. The aggregation system can then act on the determined information to help alleviate the potential outbreak by, for example, transmitting alert messages to the mobile personal medical devices integrated into the system.

FIG. 1 is a schematic illustration of a body 105 having a mobile personal medical device 100 implanted therein. The mobile personal medical device 100 can be configured for chronic in vivo implantation. Accordingly, the mobile personal medical device 100 can be sized sufficiently for implantation in any one of a number of bodily locations such as in one or more appendages. It will be understood that the mobile personal medical device will be implanted in regions that enable convenient measurement of the parameters described herein.

It will further be understood that the mobile personal medical device 100 can be configured so as to reduce a phenomenon referred to as bio-fouling which if unaddressed can lead to degradation and ultimate failure of an implanted device. Furthermore, the mobile personal medical device 100 should be fabricated using an enclosure which is bio-compatible with the surrounding environment to reduce bio-fouling as well as any potential rejection by the body. For example, the mobile personal medical device may be encapsulated in glass or other bio-compatible material while still allowing sensors to measure parameters and to communication with the mobile personal medical device. In some embodiments according to the invention, the mobile personal medical device is configured for chronic implantation such that the device 100 can be implanted for periods of at least six months without intervention.

An external sensor package for the device 100 may be about 2 mm×10 mm in the form of a rounded cylinder. This configuration may ease insertion into the body 105 when used in conjunction with a device similar to a biopsy needle. The standardization of package size and geometry may enable a diverse range of coatings such as Diamond Like Carbon (DLC) or glasses of various compositions and plastics. The inner portion of the package can be used to provide a hermetic seal isolating the device 100 from the effects of moisture and attack by the body.

As further shown in FIG. 1, a mobile personal medical device 110 can be adapted for external mounting to the body 105 whereas sensors 115 are located in vivo. Accordingly, the in vivo sensors 115 are in communication with the mobile personal medical device 110 that is outside the body 105. Although many of the embodiments described herein describe the mobile personal medical device 100 as being implanted in vivo, embodiments can also be provided where the mobile personal medical device 100 is outside the body 105 while the sensors 115 are located either in vivo or have access to the body so that the parameters described herein can be measured. For example, the sensors 115 in communication with the mobile personal medical device 110 may be provided as part of an external vest or other apparatus that may be worn. In some embodiments according to the invention, the device 100 and the sensors 115 may be integrated into an apparatus, such as a vest, that is worn, so that all components are carried by the body 105 and are not implanted in vivo.

Although FIG. 1 shows a single mobile personal medical device 100, it will be understood that multiple devices 100 can be used. For example, mobile personal medical devices 100 may be implanted in a number of different locations of the body to provide data redundancy to guard against data loss due to failure of a stand-alone device or through a catastrophic accident where the device 100 is destroyed. Accordingly, in some embodiments according to the invention, a plurality of mobile personal medical devices 10 may be used rather than the single device 100 shown in FIG. 1.

Figure 2:
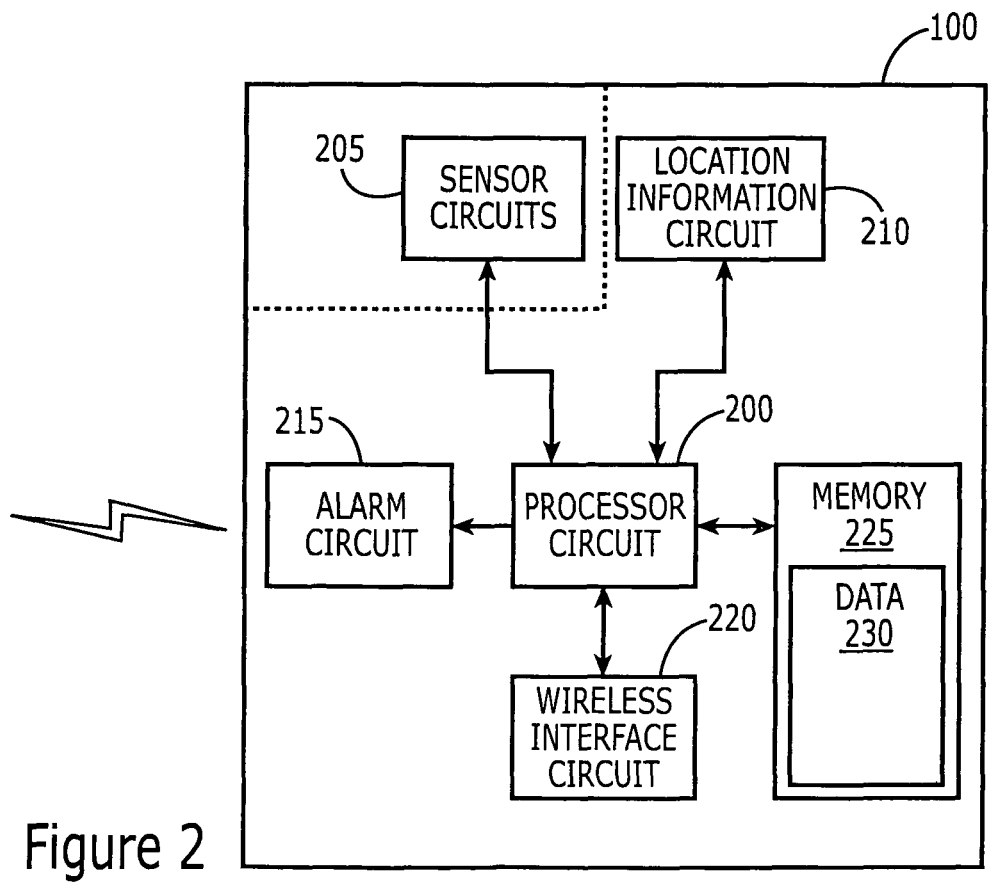
FIG. 2 is a block diagram that illustrates mobile personal medical devices according to some embodiments of the invention.

FIG. 2 is a block diagram that illustrates the mobile personal medical device 100 in some embodiments according to the invention. According to FIG. 2, a processor circuit 200 operates to coordinate the function of each of the other components shown therein. The processor circuit 200 can be any device which can be reprogrammed to coordinate the measurement of the parameters described herein over a relatively long period of time, such as six months. The processor circuit 200 is also capable of coordinating communication with remote systems or devices located outside the body. The processor circuit 200 is further configured to evaluate the measured parameters against standards and syndromes and/or other medical information stored in the mobile personal medical device 100 to determine whether a significant situation exists for the body 105. The processor circuit 200 may be implemented using special-purpose hardware, such as an Application Specific Integrated Circuit (ASIC), a gate array, a microcontroller or digital signal processor (DSP).

The mobile personal medical device 100 further includes a number of sensor circuits 205 which may be integrated into the same package as the device 100 or separately therefrom and in communication with the processor circuit 200. In some embodiments according to the invention, the sensor circuits 205 can include sensors to provide measurements regarding blood glucose level, temperature, pH, blood pressure, blood oxygen content, respiration, voice analysis, and impact force. For example, the sensor circuits 205 can include an impact sensor to record whether the body 105 has suffered a severe trauma in an automobile accident, the results of which may not be immediately evident on the exterior of the body 105. In other embodiments according to the invention, other sensors can be included in the sensor circuits 205 for the measurement of other parameters of the body 105.

The mobile personal medical device 100 includes a location information circuit 210, such as a GPS circuit found in some cell phones, which provides a geographic location of the mobile personal medical device 100. As will be appreciated by those skilled in the art, the location information circuit 210 may determine a location using a GPS receiver circuit based on any available GPS or assisted GPS based location approach in conjunction with a GPS satellite system. Such approaches are commonly referred to as assisted-GPS, which is defined, for example, in specification numbers 3GPP TS 04.31, 3GPP TS 03.71 and 3GPP TS 04.35. Assisted-GPS approaches are also discussed, for example, in U.S. Pat. Nos. 4,445,118, and 5,418,538, and 5,663,734, and 5,663,735, and 6,433,735, and in published US Patent Application No. US 2003/0011511 A1, the disclosures of which are hereby incorporated herein by reference.

The device 100 also includes a wireless interface circuit 220 that is configured to communicate with remote systems or electronic devices located outside the body 105 and with other mobile personal medical devices 100 (i.e., peers). The processor circuit 200 can use the wireless interface circuit 220 to transmit medical information from the device 100 to the remote system (such as a system configured for use in a physician's office), a device operated by an authorized EMT, and/or another device 100.

In some embodiments according to the invention, the wireless interface circuit 220 can provide an ad-hoc networking interface to enable communication with other peer devices 100 as those devices come into proximity with the device 100. For example, the wireless interface circuit 220 may be a Bluetooth™ interface that can detect other devices mobile personal medical devices 100 that have Bluetooth™ interfaces. When the device 100 is near enough to another device 100, the device 100 recognizes the proximity of the other device 100 and establishes a communication link therewith using the wireless interface circuit 220 (i.e., the Bluetooth™ interface).

Bluetooth™ is directed to providing a relatively robust high-speed wireless connection with low-power consumption and a low-cost architecture. Bluetooth™ technology may provide a universal radio interface in the 2.45 GHz frequency band to enable portable electronic devices to connect and communicate wirelessly via short-range ad hoc networks. Bluetooth™ technology is generally targeted towards the elimination of wires, cables, and connectors between such devices and systems as cordless or mobile phones, modems, headsets, personal digital assistants (PDAs), computers, printers, projectors, and local area networks. The Bluetooth™ interface is further described in an article authored by Jaap Haartsen entitled *Bluetooth—The universal radio interface for ad hoc, wireless connectivity,*

As used herein, "ad-hoc" networking refers to where devices are generally configured at the time of use based on the resources available. Such networks, typically, provide a service discovery protocol to allow, for example, identification of available resources. They may also negotiate various aspects of operations, such as peer relationships between resources, at the time of use of the resources.

In other embodiments according to the invention, the wireless interface circuit 220 can be an IEEE 80211 compliant interface that is configured to communicate with a network access point that may be included in a local area network or wide area network.

In some embodiments according to the invention, the wireless interface circuit 220 can be a RadioFrequency ID type interface (RFID). It will be understood that the RFID interface provided by the wireless interface circuit 220 can be either active or passive. In a passive RFID interface, the device 100 may be activated by a remote RFID scanner that can provide power to the device 100 to activate the wireless interface circuit 220 for transmission of medical information to/from the device 100. In some embodiments according to the invention, the RFID interface provided by the wireless interface circuit 220 can be an active RFID circuit that is continuously powered and transmits the medical information without excitation from an external scanner needed. Other types of wireless interfaces may be used to communicate with remote systems or devices including the physician's system and EMT systems described herein.

In operation, information stored in the device 100 can be "read" by transmitting an RF signal from an RFID interface of the remote system to energize an RF antenna associated with the wireless interface circuit 220, if the tag is within transmit range of the remote system. Once energized, the wireless interface circuit 220 can transmit an RFID signal including the medical information stored in the device 100. It will be understood that the energy imparted to the antenna can be used to power the tag transmitter circuit and ancillary circuits used by the wireless interface circuit 220 to transmit. Accordingly, the device 100 may not require a battery or other onboard power source to necessarily transmit, which is sometimes referred to as passive RFID tags. RFID is discussed further on, for example, the Internet at idtechex.com/pdfs/en/O7289Z3822.pdf, which is hereby incorporated herein by reference.

The mobile terminal 20 includes a location determination circuit 260 that is configured to determine the location information for a movable object based on the ID information received from the moveable object via an RFID interface circuit 265. In some embodiments according to the invention, the location determination circuit 260 is a Global Positioning System (GPS) location circuit, including a GPS receiver circuit, that uses, for example, any available GPS or assisted GPS based location approach in conjunction with a GPS satellite system 274. Such approaches are commonly referred to as assisted-GPS, which is defined, for example, in specification numbers 3GPP TS 04.31, 3GPP TS 03.71 and 3GPP TS 04.35. Assisted-GPS approaches are also discussed, for example, in U.S. Pat. Nos. 4,445,118, and 5,418,538, and 5,663,734, and 5,663,735, and 6,433,735, and in published US Patent Application No. US 2003/0011511 A1, the disclosures of which are hereby incorporated herein by reference.

In some embodiments according to the invention, the wireless interface circuit 220 can be used to transmit an emergency message to nearby electronic devices, such as cell phones, PDAs, etc. Accordingly, the processor circuit 200 may utilize the wireless interface circuit 220 to transmit emergency messages to other electronic devices within range of the interface circuit 220. For example, the processor circuit 200 may transmit a message over the wireless interface circuit 220 to a nearby cell phone using a Bluetooth interface, whereby a message may be displayed on the cell phone that a nearby person is experiencing a medical emergency. Similar type communications may be provided to laptops, PDAs, or other electronic devices having displays.

The device 100 also includes an alarm circuit 215 that can be activated by the processor circuit 200. The alarm circuit 215 is configured to alert the person and/or those nearby that the person with the implanted device 100 is experiencing a possible emergency or may otherwise be in distress. In some embodiments according to the invention, the alarm circuit 215 is an audible and/or a visible alert, such as a tone coupled with a light.

As further shown in FIG. 2, the device 100 also includes a memory 225 that stores data 230, which can be written and read by the processor circuit 200. The memory 225 may include any memory devices containing the software and data used to implement the functionality in accordance with embodiments of the present invention. The memory 225 can include, but is not limited to, the following types of devices: cache, ROM, PROM, EPROM, EEPROM, flash memory, SRAM, DRAM and magnetic disk. The memory 225 may include several categories of software to provide operation of the profile manager 110: an operating system; application programs including the software to receive measured parameters and incorporate those measurements into previously received values, input/output device drivers, etc. The memory 225 can also include data that is used to coordinate the operations of the circuits shown therein as well as an operating system to govern the overall function of the device 100.

Figure 3:
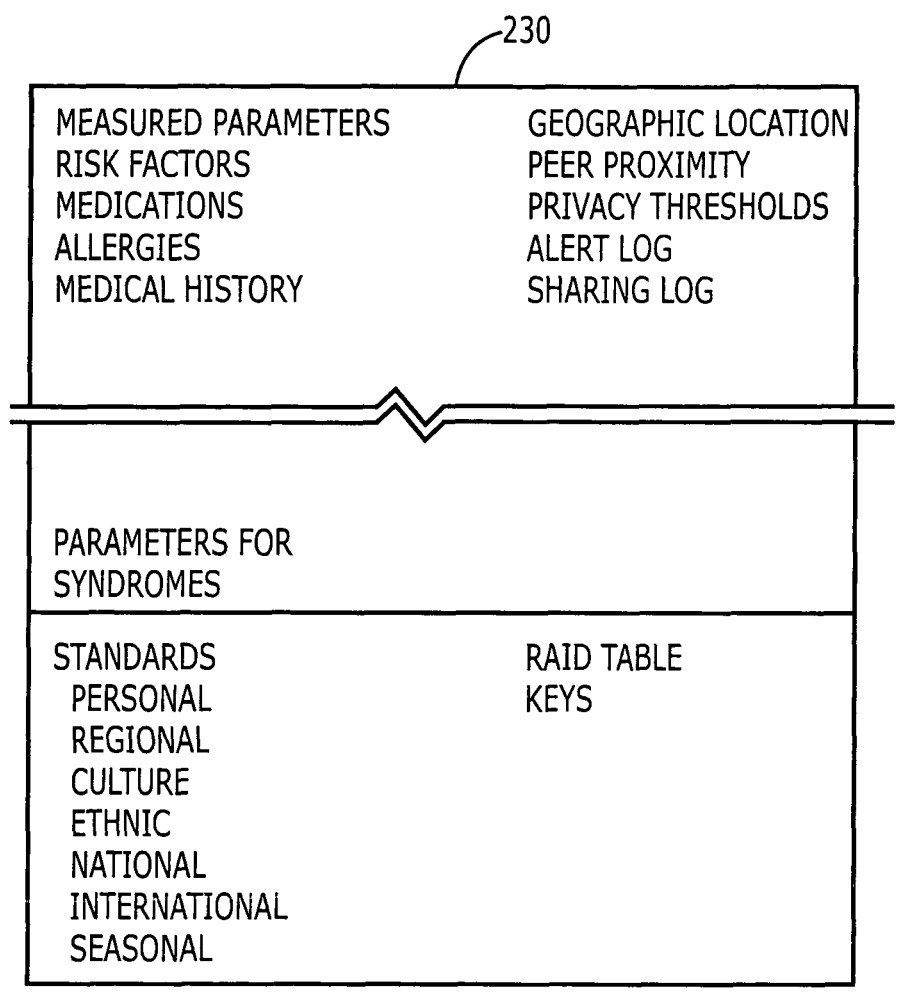
FIG. 3 is a schematic representation of data maintained by mobile personal medical devices and persistent storage devices according to some embodiments of the invention.

The data 230 can further include medical information that is relevant to the body 105 and can be used by the processor circuit 200 to determine whether the body 105 is exhibiting a syndrome, such as a syndrome known to be associated with the body or another type of syndrome which is known, but has not been previously associated with the body 105. In particular, according to FIG. 3, the memory 225 stores the data 230, which can include measured parameters that represent measurements received by the device 100 from the sensor circuits 205 for the bodily functions monitored. For example, the parameters measured can include blood pressure, blood glucose, PH, temperature, respiration, voice analysis, impact force, PH, etc. The measured parameters can be stored as they are received or can be processed to provide a statistical indication of the history of the measured parameters. For example, the measured parameters can include an average for each of the parameters measured over a specified period of time. In some embodiments according to the invention, the measured parameters can include both a instantaneous as well as a historical value over different lengths of time.

The data 230 also includes risk factors known to be associated with the body, which can complicate the occurrence of events or can increase the likelihood that events can occur. Risk factors can include, for example, excessive smoking, drinking, and other lifestyle factors, etc. The data 230 can also include a record of medications that the body 105 is currently being administered. The medications can be important when, for example, an emergency medical provider is intervening to provide care or can be used to analyze the measured parameters.

The data 230 can also include a record of allergies which have been identified associated with the body 105. The allergies can be used in the analysis of the measured parameters (in conjunction with the other factors described here) to set a threshold to be associated with the measured parameters. The data 230 can also include a medical history associated with the body 105 which includes all past medical events, all previous treatments, medications, syndromes, treating physicians, accreditations thereof, etc.

The data 230 can also include data indicating geographic location of the mobile device 100 so that, for example, a remote system can analyze the movements of the body 105 throughout an environment and attempt to correlate those movements with an observed syndrome. The data 230 can also include peer proximity information which indicates which peer devices the current device 100 has been in close proximity to. Such information may be important in predicting and/or monitoring the outbreak of communicable diseases and may further be used in contacting persons who may have been in close contact with others that have been diagnosed with a particular syndrome.

The data 230 also includes privacy thresholds for any of the medical information described herein. In particular, the privacy threshold can indicate that any information having a lower privacy code is not to be transmitted whereas information having a higher privacy code is transmitted. For example, if a particular piece of medical information has a privacy code that exceeds a privacy threshold, the medical information would not be transmitted or accessed in the device. However, if the privacy threshold is raised to exceed the privacy code of the medical information, the medical information may then be transmitted or accessed.

The data 230 also includes an alert log which records events (and other ancillary information such as time) where an alert (either audible, visible, or a broadcast message) was generated by the device 100. The data 230 also includes a sharing log which records all access to the medical information included in the device 100. For example, the sharing log can record when the device 100 transmits medical information from the device 100 and when the device 100 is accessed by a remote system (such as a system operated in a physician's office) or device.

The data 230 also includes parameters associated with syndromes (both syndromes known to be associated with the body as well as syndromes which are not known to be previously associated with the body). For example, the values for the measured parameters can define profiles which may indicate the existence of particular syndromes, such as SARS. Therefore, when the measured parameters correlate to the parameters known to be associated with SARS, the medical device 100 may determine that an alert should be generated based on the likelihood that the body 105 is experiencing symptoms similar to SARS.

The data 230 can also include standards for the measured parameters against which those measured parameters can be evaluated. For example, the standards can include personal standards that are based on the measured parameters over an extended period of time, a regional standard which is based on medical studies for people located within a particular region of the country of world, cultural standards which can provide parameter values according to a culture or subculture in which the individual lives, ethnic standards which can indicate parameters known to be associated with individuals having a particular ethnic background, national standards, such as those determined by a national medical board and international standards. It will be also understood that the data 230 can include values for seasonal variations that change these standards based on particular times of the year or weather. The data 230 can also include shared keys that are generated by the device 100 in conjunction with the remote system, such as that that may be operated in a physician's office.

The data 230 can also include a Redundant Array of Independent (or Inexpensive) Disks RAID table that indicates the level of raid protection offered by the devices 100 associated with the body 105. For example, the RAID table may indicate that the devices are configured so that data and parity bits are stored across a plurality of devices 100 that are implanted in vivo in the body 105. If a particular device fails or is lost due to a catastrophic accident, the medical information including the measured parameters may be rebuilt based on the data stored in the remaining devices 100 and the parity bits.

RAID indicates a category of storage using two or more devices in combination for fault tolerance. There are number of different RAID levels, the most common of which are designated as Levels 0, 3, and 5. Level 0 provides data striping (spreading out blocks of each file across multiple devices) but no redundancy. This may improve performance but does not deliver fault tolerance. Level 1 provides disk mirroring, Level 3 is the same as Level 0, but also reserves one dedicated device for error correction data, which can provide some level of fault tolerance. Level 5 provides data striping at the byte level and also stripe error correction information, which can provide good fault tolerance. Other types of RAID protection are known and available.

Figure 4:
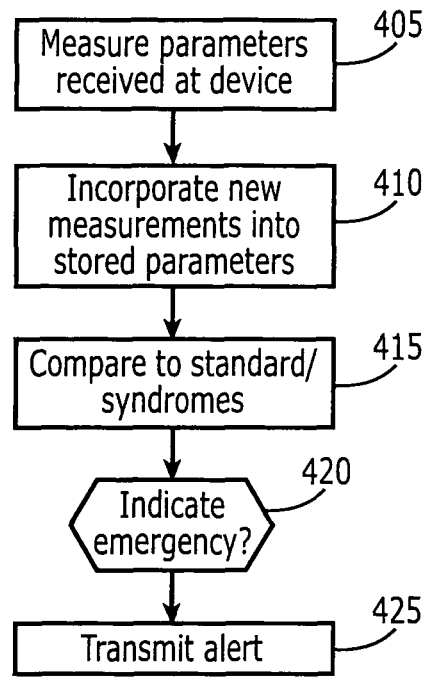
FIGS. 4-6 are flowcharts that illustrate operations of mobile personal medical devices in some embodiments according to the invention.

According to FIG. 4, the processor circuit 200 receives the measurement of parameters monitored by the sensor circuits 205 and stores the measured parameters as data 230 in the memory 225 (block 405). Over time, the processor circuit 200 incorporates the measurements of the parameters into the measurements already stored in the memory 225 (Block 410). For example, the processor circuit 200 may average the measured parameters with the previously stored parameters as well as maintain an ongoing record of the instantaneous measurements received. Although the incorporation of the new measurements into the parameters is described herein in terms of averaging those parameters with the previously stored parameters, other types of statistical analysis and processing can be used to provide an accurate indication of the parameters at a particular time.

The measured parameters (having been incorporated into the previously measured parameters) are compared to the stored standards and/or syndromes (block 415). The comparison of the measured parameters to the standards/syndromes can be done by correlating the measured parameters to the parameters associated with the syndromes. For example, a correlation may be performed between the respective parameters for SARS or Avian Flu and the parameter values collected by the device 100. If the measured parameters correlate well with the parameters known to be associated with any of the stored syndromes, a determination may be made that the body 105 may have been exposed and is exhibiting symptoms associated therewith.

Alternatively, the comparison can be performed by comparing the measured parameters to the standards (i.e., the personal, regional, cultural, ethnic, national and international standards) maintained by the device 100 to determine whether the measured parameters exceed any of these standards. For example, if any of the measured parameters exceeds any or all of the standards for more than a predetermined time threshold, it may be determined that the measured parameters are unacceptably high and, therefore, an alert may be warranted.

It will be further understood that some of the parameters may be weighted more heavily than others in determining the correlation between the stored syndromes and the measured parameters. For example, blood glucose may be a highly relevant parameter for a person known to have a diabetic condition. Accordingly, the parameter can be weighted differently in determining the comparison between the measured parameters and the stored syndromes and/or the standards. Furthermore, the other medical information (such as risk factors, medications, allergies, medical history, etc.) can be used to weight some of the parameters more or less than would otherwise be done. For example, if a risk factor of smoking is known to be associated with the body 105, blood pressure may be particularly important in determining whether a particular syndrome is correlated to the measured parameters.

Furthermore, the medical history may indicate the value of measured parameters previously associated with past events. For example, the medical history for the body 105 may indicate that a particularly high blood oxygen level was previously observed during a past emergency. Accordingly, a measured value for the blood oxygen may be particularly relevant in determining correlation between a syndrome and the measured parameters. The same can be true for the medications, allergies, etc. that are known to be associated with the body 105 such that particular parameters may be weighted more or less depending on what those known medications/allergies are.

Once the comparison has been performed, the device 100 may indicate an emergency (block 420) and thereby transmit an alert signal (block 425) from the device. As described herein, the alert signal may be an audible and/or visible alert to notify the body 105 or persons nearby that the person is maybe experiencing a medical emergency. Alternatively (or in combination with the audible/visible alert), the alert signal may be an electronic signal transmitted to a nearby electronic device, such as a cell phone, PDA or laptop, indicating that someone nearby is in distress and may further indicate the nature of the emergency determined by the comparison to the standards/syndromes. It will be further understood that the alert signal transmitted by the device 100 may be received by a network access point which may then be relayed over a wide area or local area network.

Figure 5:
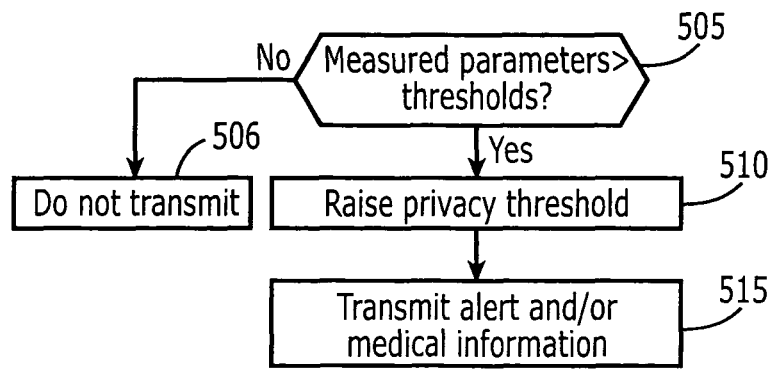

FIG. 5 is a flowchart that illustrates operations of the device 100 in indicating an emergency according to some embodiments of the invention. According to FIG. 5, if any of the measured parameters exceeds a predetermined emergency threshold for any of the parameters for a specified period of time and/or by a specific amount (block 505), the device 100 determines that medical information and/or an alert signal should be transmitted. If, on the other hand, no emergency has occurred no information is transmitted from the device 100 (block 506). Accordingly, if the medical information is to be transmitted (block 505), the processor circuit 200 raises a privacy threshold (block 510) intended to protect the privacy of the medical information stored in the device 100 so that at least some medical information can be transmitted along with the alert signal from the device 100 (block 515).

The medical information transmitted from the device 100 can be transmitted in an order according to the priority of the medical information therewith. For example, the processor circuit 200 may determine that the blood glucose level is the highest priority medical information to be transmitted along with the alert signal. Accordingly, the processor circuit 200 may transmit the recorded values for the blood glucose level from the device 100 along with the alert signal (block 515). In some embodiments according to the invention, only the relevant medical information that does not exceed the privacy threshold is transmitted so that other higher privacy medical information is protected.

It will be further understood that rather than determining that an emergency exists, the processor circuit 200 may determine that the measured parameters nonetheless indicate a serious situation which may worsen over time and, therefore, may elect to transmit information despite the fact that the measured parameters have not reached the level deemed to be an emergency. Accordingly, the processor circuit 200 may lower the privacy threshold enough to allow the transmission of only selected portions of the medical information, rather than a more complete set of medical information as described above in reference to an emergency situation.

Figure 6:
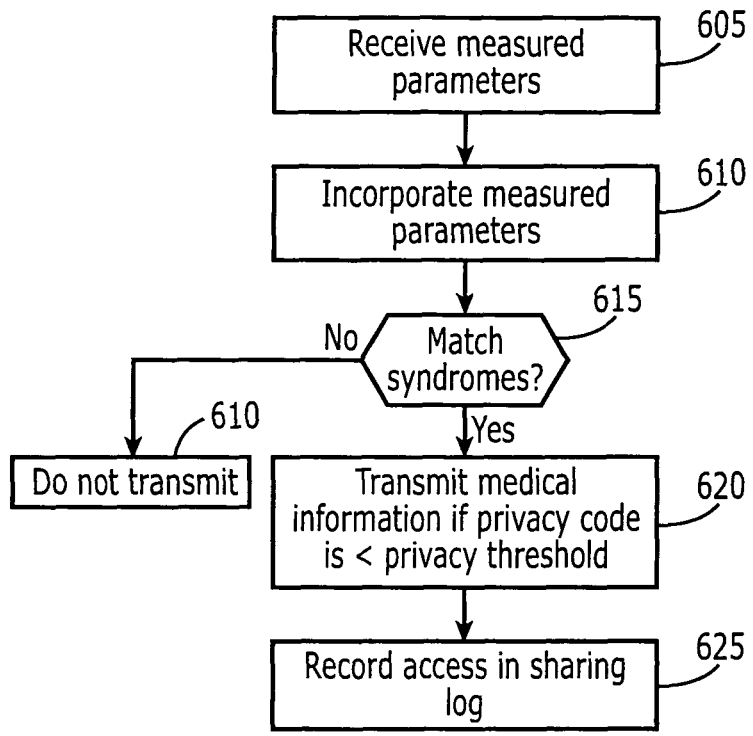

FIG. 6 is a flowchart that illustrates operations of the device 100 to correlate the measured parameters with syndromes according to some embodiments of the invention. According to FIG. 6, the measured parameters are received by the device 100 (block 605), and are incorporated into the stored values for the parameters (block 610) for comparison to parameters that are associated with the stored syndromes (block 615). It will be understood that the correlation or matching between the parameters known to be associated with syndromes and the measured parameters can be provided as described above by, for example, weighting some of the parameters more heavily than others and thereby relying on closer correlation among a subset of parameters rather than the entire set of parameters measure. Furthermore, some of the parameters may be more heavily or less heavily weighted dependent on risk factors, medications, allergies, and the other information stored in the device 100 as part of the data 230.

It will be understood that the correlation can be performed using well known techniques, such as cross-correlation, auto-correlation, and the like. The correlation can be used to compare individual values of the parameters and/or a series of values for the parameters. For example, the parameters associated with a syndrome can include values for a specified period of time, such as 24 hours, so that the series of measured parameters received by the device 100 over the 24 hour period can be compared to the corresponding values associated with the syndrome. Such values may show, for example, the normal profile of a blood glucose level for a person fitting the physical parameters (such as height, weight, age, gender, etc.) with diabetes.

If the measured parameters correlate with at least one of the stored syndromes (block 615), the device 100 can transmit medical information associated with the correlated syndrome if the privacy codes associated with each of the individual pieces of medical information are less than the privacy threshold (block 620). Furthermore, the device 100 records the transmission of the medical information from the device 100 in the sharing log included in the data 230 (block 625). If, on the other hand, the measured parameters do not correlate with at least one of the stored syndromes (block 615), the device 100 does not transmit the medical information (block 610).

Figure 7:
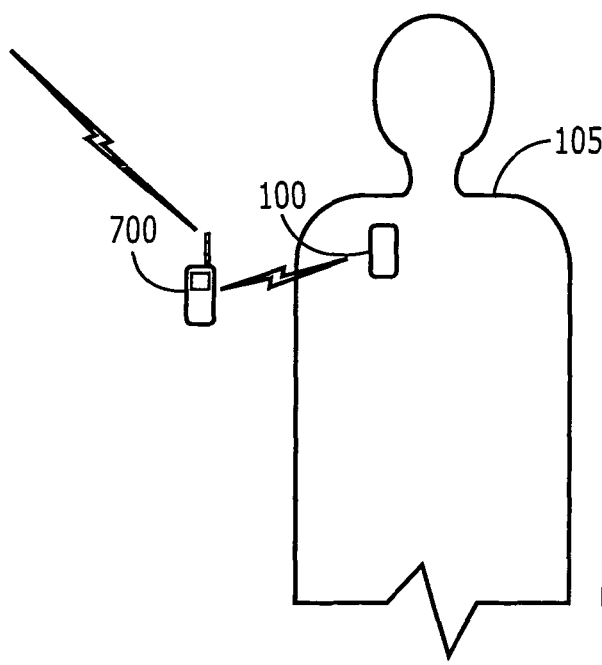
FIG. 7 is a schematic representation of an in vivo mobile personal medical device configured to communication with a remote electronic device in some embodiments according to the invention.

FIG. 7 is a schematic illustration of the body 105 including a device 100 that is configured to be in communication with a remote electronic device 700, such as a cell phone, PDA, laptop, etc. In some embodiments according to the invention, the device 100 can transmit a message to the electronic device 700 over any wireless interface supported by the wireless interface circuit 220. For example, the message transmitted by the device 100 to the electronic device 700 can be a message intended for the display of the electronic device 700 or a message that is to be relayed to a wireless network.

It will be further understood that the transmission from the device 100 to the electronic device 700 can include the medical information as described above in reference to FIGS. 4-6, such as when an emergency situation occurs where the electronic device 700 is to provide a message thereon warning a viewer that the body 105 is experiencing a serious medical event. Furthermore, in some embodiments according to the invention, the electronic device 700 may be associated with the body 105 and utilized to relay the message or periodic information to a remote system for storage on a persistent storage device included therein. For example, the electronic device 700 may be located proximate to the device 100 so that the received parameters can be periodically relayed to the persistent storage system or a system which is otherwise intended to monitor the parameters collected by the device 100. In some embodiments according to the invention, the electronic device 700 is a public sensor that can be coupled to an aggregation system as described herein in reference to FIGS. 16 and 17. In still other embodiments according to the invention, the electronic device 700 is capable of transmitting to the device 100 including messages from an aggregation system to alert the body 105 to exposure.

Figure 8:
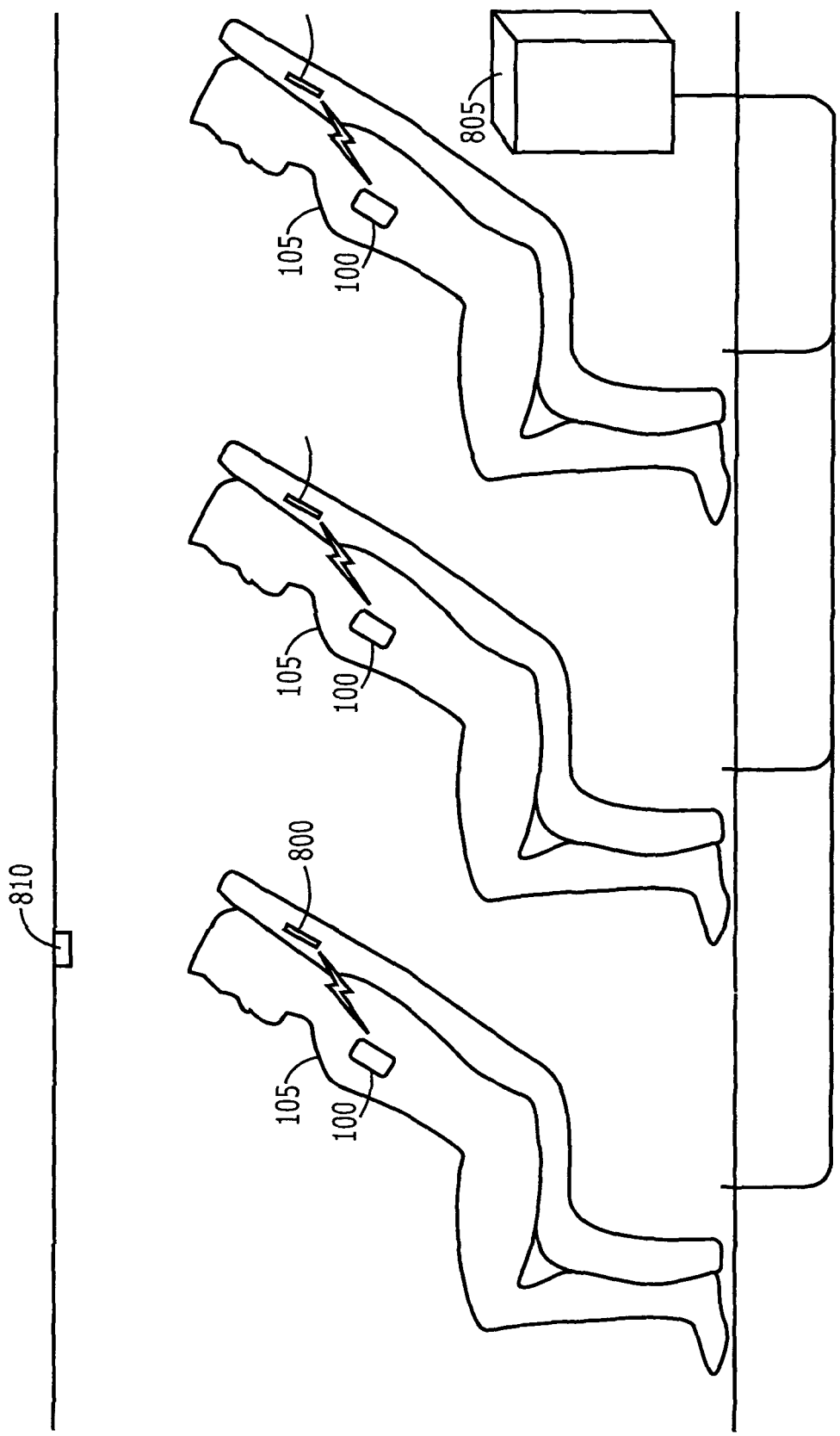
FIG. 8 is a schematic representation of a remote electronic device included in airline seat and configured for communication with an in vivo mobile personal medical device in some embodiments according to the invention.

FIG. 8 is a schematic representation of the device 100 implanted in vivo in the body 105 and configured to be in communication with an electronic device 800 that is embedded within a seat in an airliner cabin. It will be understood that in these embodiments according to the invention, that the signal emitted by the device 100 can be relatively low frequency and/or have relatively low power spectral density to reduce potential interference between transmissions from the device 100 and an aircraft's communication and navigation systems. In operation, the electronic device 800 can receive signals from the device 100 which can then be relayed to an onboard monitoring system 805, whereby a member of the crew may be alerted to an emergency being experienced by the body 105 including a particular seat number from which the alert was received. In some embodiments according to the invention, the electronic device 800 is further in communication with an attendant call signal 810 which provides a general visual indication that the body 105 may be in need of assistance if, for example, an emergency or serious medical situation has arisen as indicated by the transmission from the device 100.

Figure 9:
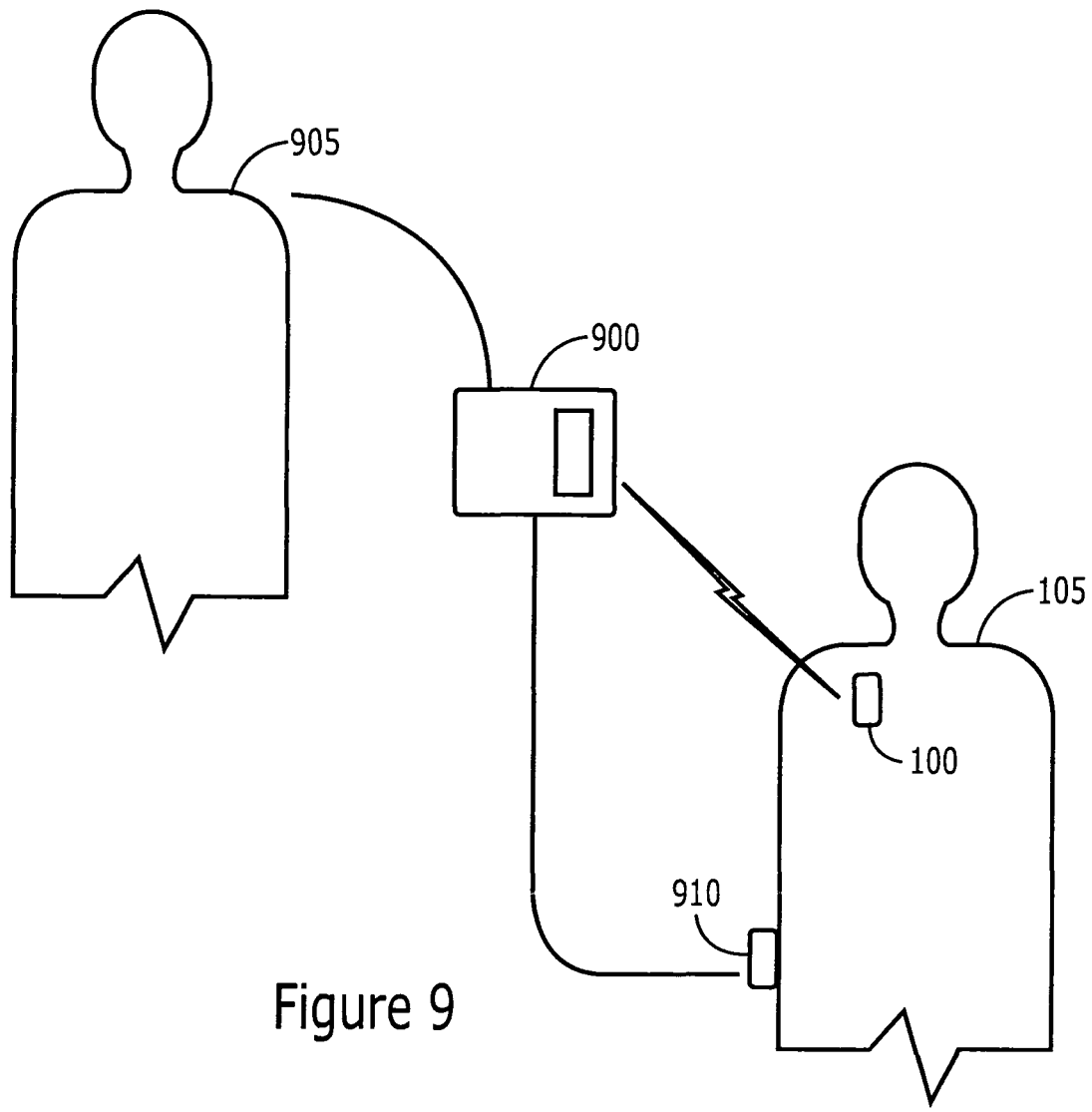
FIG. 9 is a schematic representation of an in vivo mobile personal medical device configured for communication with a recognized medical device operated by an authorized emergency medical provider in some embodiments according to the invention.

FIG. 9 is a schematic representation of the device 100 implanted in vivo in the body 105 and in communication with a recognized emergency medical device 900 operated by an authorized user (such as an EMT) 905 in some embodiments according to the invention. According to FIG. 9, the EMT 905 establishes a privacy relationship with the recognized emergency medical device 900 by, for example, logging onto the device 900 using an authentication code associated with the EMT 905.

The device 100 communicates with the device 900 to establish a privacy relationship therebetween so that the device 100 can upload medical information to the device 900 while maintaining the privacy of the medical information. Accordingly, the EMT 905 can administer emergency assistance to the body 105 with the advantage of the medical information provided by the device 100 even though the body 105 may be unresponsive. Furthermore, other recognized medical devices 910 may be used in conjunction with the device 900 to provide further medical information regarding the status of the body 105.

Figure 10:
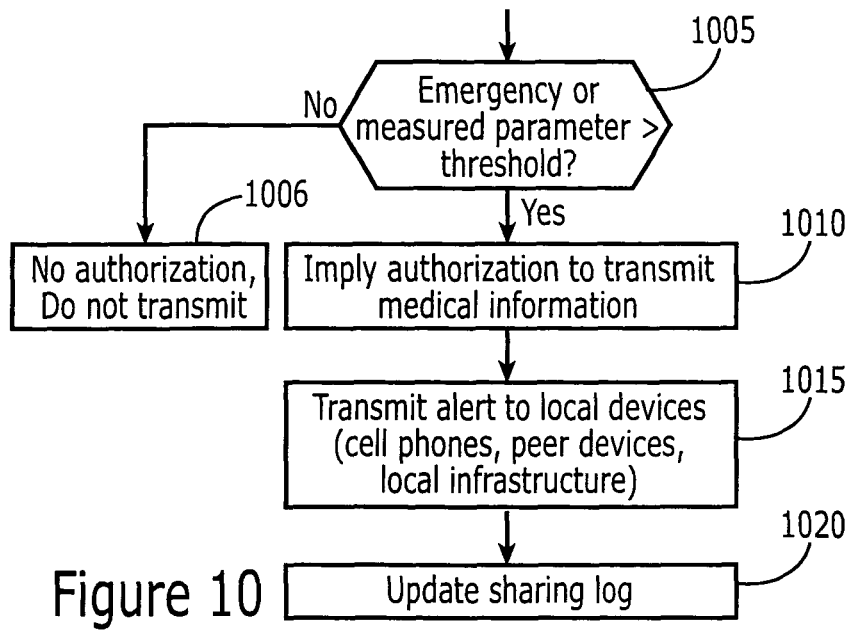
FIGS. 10-11 are flowcharts that illustrate operations of mobile personal medical devices in communication with remote electronic devices including recognized medical devices in some embodiments according to the invention.

In operation as shown according to FIG. 10, if the device 100 determines that an emergency situation exists or that a measured parameter has exceeded a specified threshold for a certain period of time (block 1005), an implied authorization may be assumed between the device 100 and the device 900 due to the fact that an emergency or a serious situation has been detected (block 1010). If, on the other hand no emergency exists (block 1005), no authorization is granted (block 1006). The emergency or serious medical situation determined by the device 100 can, therefore, provide the implied authorization for the device 900 to access the medical information stored in the device 100. Accordingly, the device 100 transmits the medical information to the recognized medical device 900 for further analysis (block 1015). Furthermore, the device 100 records the access to the medical information by the recognized medical device 900 by updating the sharing log (block 1020).

Figure 11:
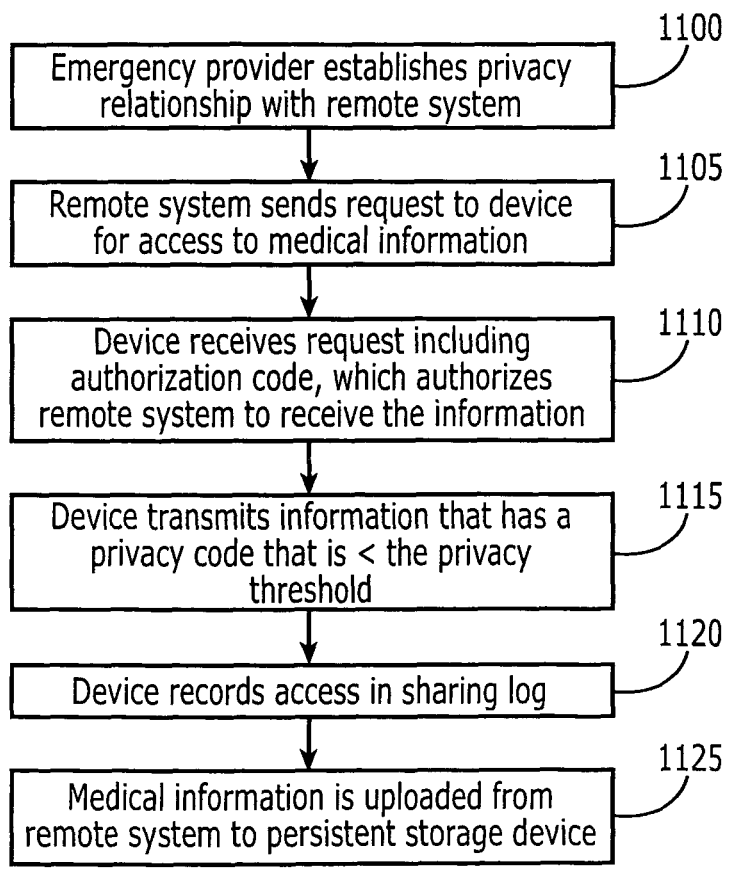

FIG. 11 is a flowchart that illustrates operations of the mobile personal medical device 100 transmitting medical information to a remote system in a non-emergency situation in some embodiments according to the invention. According to FIG. 11, an emergency medical provider establishes a privacy relationship with the remote system, which is a recognized medical device as illustrated by device 900 in FIG. 9 (block 1100). The privacy relationship with the remote system can be established when the emergency medical provider logs onto the device 900 using, for example, an emergency medical provider authorization code. The remote system sends a request to the device 100 to transmit the medical information to the remote system (block 1105). It will be understood that the request from the remote system can include the emergency medical provider authorization code which the emergency medical provider inputs into the remote system.

The device 100 receives the request from the remote system including the code which authorizes the remote system to receive the medical information (block 1110). It will be understood that even though the authorization code provided by the emergency medical provider may authorize access to some of the medical information stored in the device 100, the code may not authorize the device 100 to transmit all of the medical information to the remote system. In particular, some of the medical information may have a privacy code associated therewith which is still greater than the privacy threshold stored within the device 100. In still other embodiments according to the invention, the authorization code provided by the emergency medical provider may authorize the device 100 to raise the threshold so that additional medical information is authorized to be received by the remote system.

The device 100 transmits the medical information requested by the remote system which has a privacy code that is less than the privacy threshold (block 1115). The device 100 then records the transmission of medical information to the remote system along with the emergency medical provider authorization code that accompanied the request (block 1120). The medical information can then be uploaded from the remote system to a persistent storage device for long term storage of the medical information accessed during the event (block 1125).

Although the description above in reference to FIG. 11 illustrates authorization provided for the remote system to access the medical information using an authentication code provided by an emergency medical provider, it will be understood that in other embodiments according to the invention, the emergency medical provider or recognized medical device may provide a copy of the shared key that is stored in the memory of the device 100. Upon receipt of the shared key, the device 100 can authorize the remote system to access the medical information stored therein as described above.

As shown in FIG. 9 above, authorization for access to the medical information in the device 100 is implied due to the nature of the emergency wherein, for example, the body 105 may be unresponsive. In contrast, operations described above in reference to FIG. 11 illustrate that authorization can be provided by a key or code provided by the emergency medical provider to authorize access to the medical information stored in the device 100.

Figure 12:
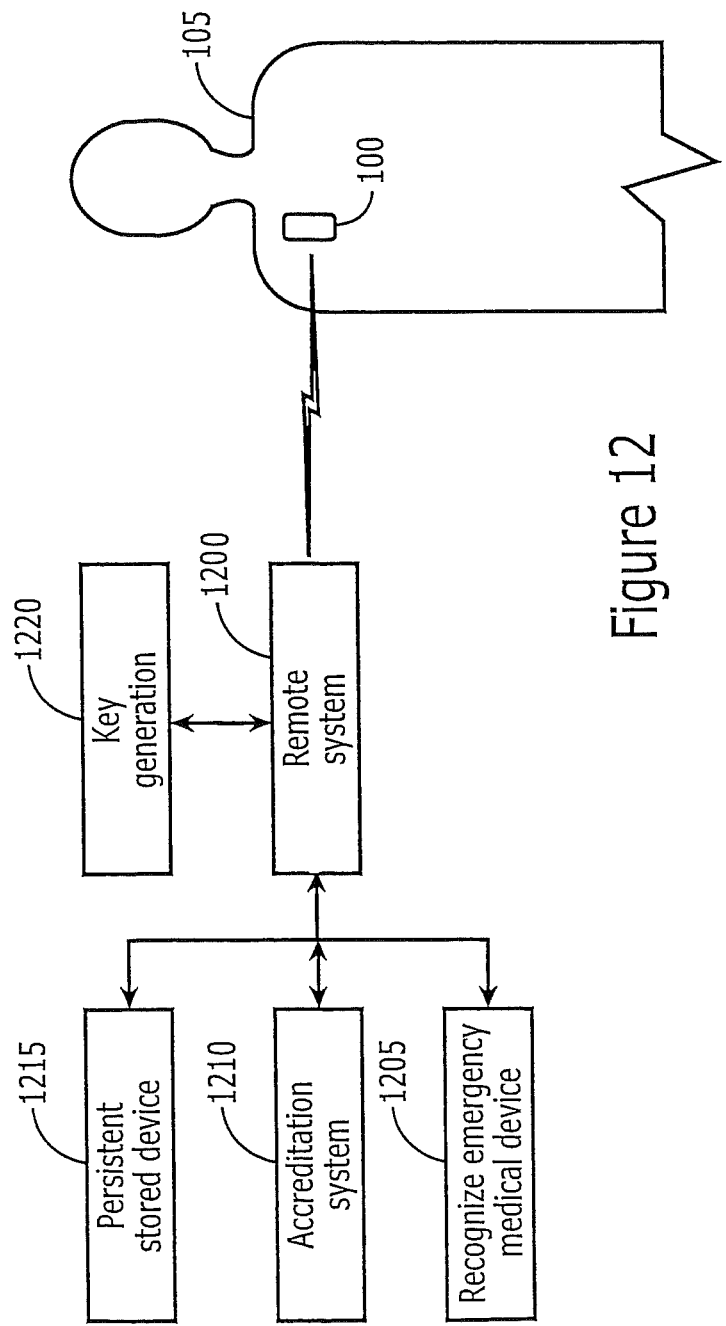
FIG. 12 is a schematic representation of a remote system configured for operation by a medical provider for communication with mobile personal medical devices in some embodiments according to the invention.

FIG. 12 is a schematic representation of a remote system, which may be operated by a medical provider such as a physician, configured to access medical information stored in the device 100 implanted in the body 105 in some embodiments according to the invention. In particular, the remote system 1200 is configured to access the medical information stored in the device 100 via wireless communication via the wireless interface circuit 220 in the device 100. The remote system 1200 may provide essentially the same communications as the systems described above in reference to FIGS. 8 and 9, which are capable of requesting that the device transmit the medical information.

The system shown in FIG. 12 further includes a key generation circuit 1220 that operates under the control of the remote system 1200 to generate a shared key that is stored within the remote system 1200 and can be downloaded to the device 100 for storage therein. The system in FIG. 12 also includes a persistent storage device 1215 which can store medical information uploaded from the device 100 and the shared key generated by the key generation circuit 1220. The system in FIG. 12 also includes access to an accreditation system 1210 which lists the accreditation for medical providers that may provide medical services to the body 105 over an extended period of time. The system in FIG. 12 also includes access to a recognized emergency medical device 1205, such as that described in reference to FIG. 9. Access to the recognized emergency medical device can be used to upload medical information retrieved in the field to the persistent storage device 1215 so that the medical information may be later accessed and analyzed. It will be understood that the term "key" as used herein can refer to a generated key pair, where one key of the pair remains private and the other key in the pair is made publicly available. Furthermore, the keys can be generated and used in accordance with the approaches discussed in US Patent Publication No. 20060206361, entitled System For Maintaining Patient Medical Records For Participating Patients, by Logan, the entirety of which is incorporated herein by reference.

Figure 13:
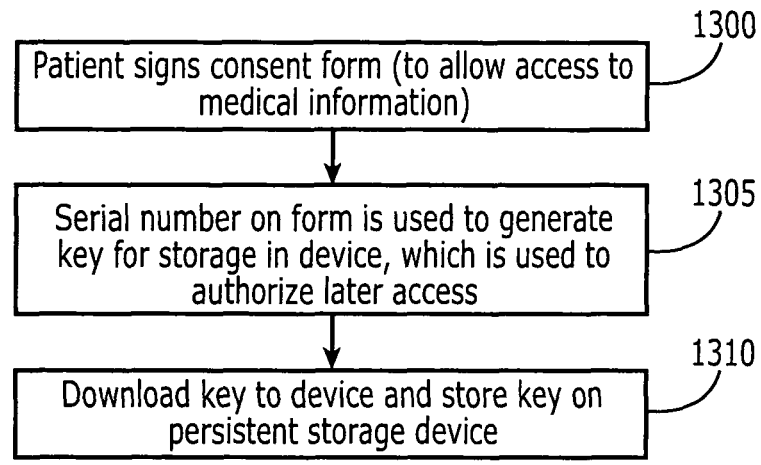
FIGS. 13-15 are flowcharts that illustrate operations of remote systems in conjunction with mobile personal medical devices in some embodiments according to the invention.
Figure 14:
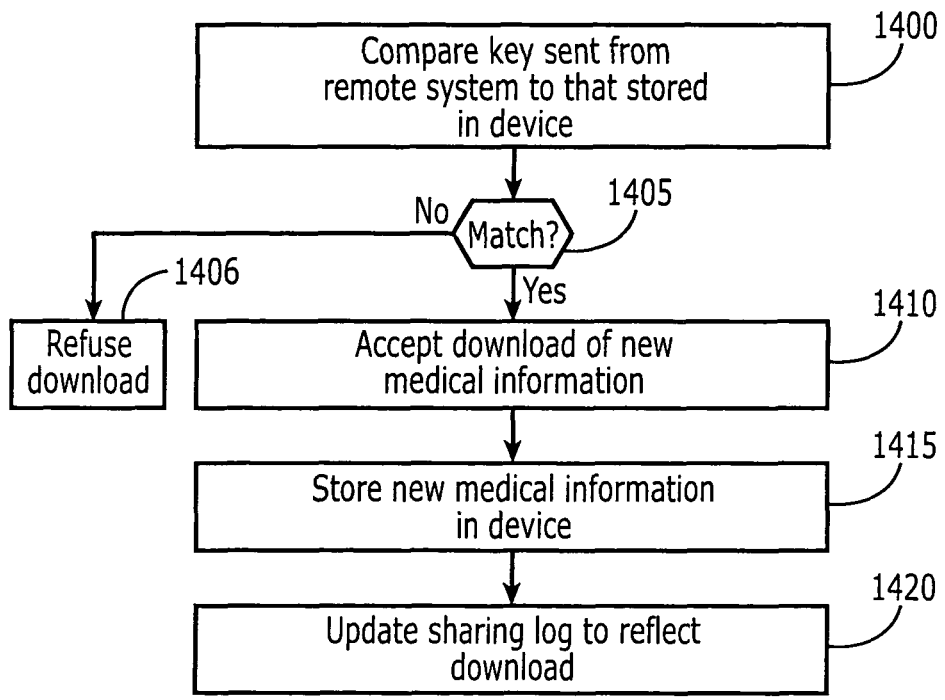
Figure 15:
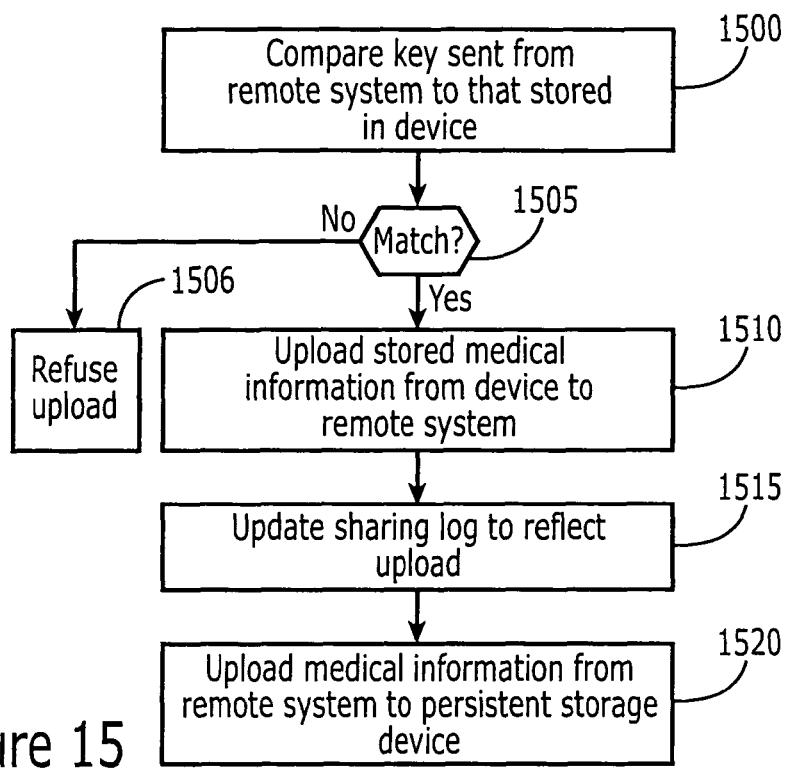

In operation, the system shown in FIG. 12 can be utilized according to the flowcharts shown in FIGS. 13-15. According to FIG. 13, a patient (i.e., the body 105) can sign a consent form which authorizes the operator of the system in FIG. 12 to access medical information stored in the device 100 (block 1300). A serial number on the form can be used to generate a shared key using the key generation circuit 1220 for storage in the device 100 (block 1305). The shared key can be used to authorize subsequent access to the medical information in the device 100. The shared key is also stored on, for example, the persistent storage device 1215 or, alternatively, on local storage associated with the remote system 1200 (block 1310).

According to FIG. 14, the device 100 compares the shared key sent from the remote system to the shared key stored within the device 100 (block 1400). If the shared keys match (block 1405), the download of new medical information is accepted (block 1410) and the new downloaded medical information is stored in the device 100 (block 1415). The device 100 also updates the sharing log to record access to the stored medical information (block 1420). If the shared keys do not match, the access is denied (block 1406).

It will be understood that the new medical information downloaded from the remote system can represent updated versions of the information previously stored as part of the medical information in the device 100. For example, the downloaded medical information may include new values for standards or entirely new standards altogether. The downloaded medical information may also include updated risk factors, allergies, new medications prescribed to the patient, as well as additional medical history that was collected during the time interval between the current download and the previous download, such as when the patient previously visited the physician's office.

The additional medical history may include previous field events where the body 105 received an emergency medical treatment in the field whereupon medical treatments not stored in the device 100 were uploaded to the persistent storage device 1215 and now subsequently downloaded into the device 100 through the remote system 1200. The downloaded information may also include new types of syndromes or revised parameters that are associated with those known or new syndromes. The new medical information can also include new processes to be used for the correlation of the measured parameters to the syndromes.

FIG. 15 is a flowchart that illustrates operations of the device 100 in conjunction with the remote system 1200 to upload stored medical information in some embodiments according to the invention. According to FIG. 15, the shared key provided by the remote system to the device 100 is compared to the shared key stored therein (block 1500). If the shared keys match (block 1505), medical information stored in the device 100 is uploaded to the remote system including all the measured parameters recorded since the device 100 was last accessed (block 1510). If, however, the keys to not match (block 1505), access to the device 100 is refused (block 1506).

The medical information uploaded to the remote system can include all the recorded measured parameters as well as the geographic location information, peer proximity, alert logs, and sharing logs. Furthermore, additional medical information can be uploaded in, where, for example, the patient has been treated by another physician during the time interval between accesses by the remote system. For example, the patient may have visited an allergy specialist prior to the visit to the current physician wherein the allergist downloaded into the device 100 including information regarding the diagnosis of allergies for the patient. The device 100 then updates the sharing log to reflect the current access to the medical information stored in the device 100 (block 1515). In some embodiments according to the invention, the uploaded information can be sent from the remote system to the persistent storage device 1215 (block 1520).

Figure 16:
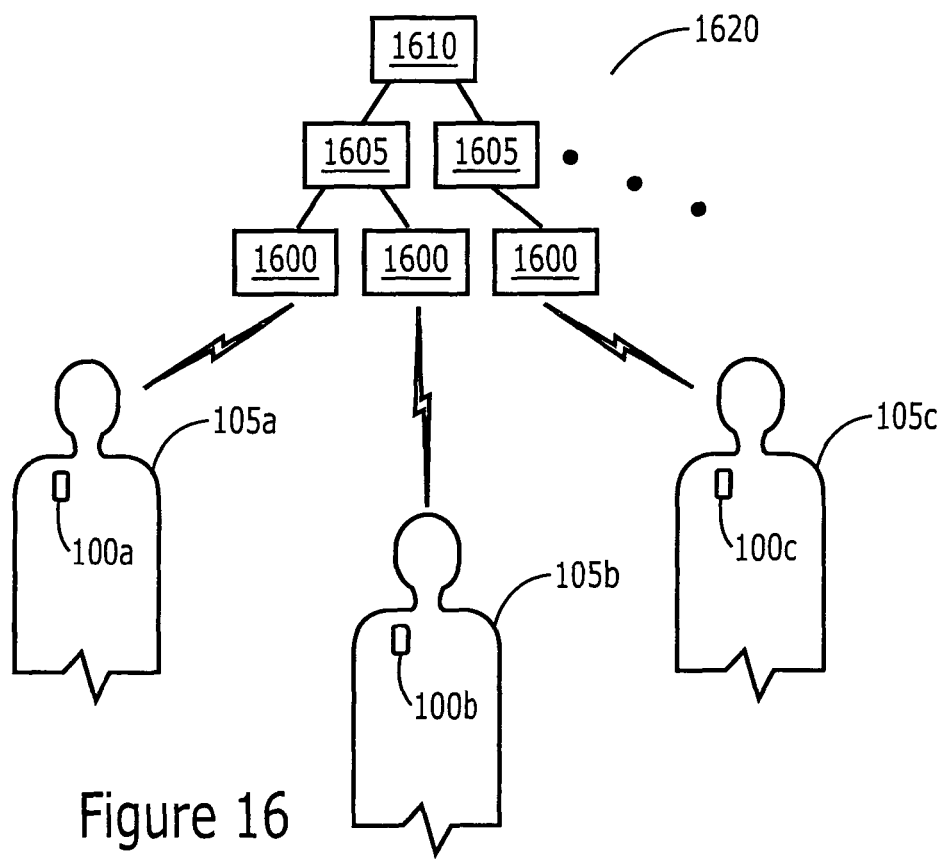
FIG. 16 is a schematic representation of an aggregation system in communication with a plurality of mobile personal medical devices in some embodiments according to the invention.

FIG. 16 is a schematic illustration of an aggregation system 1620 including devices 100A-C configured to operate therein in some embodiments according to the invention. According to FIG. 16, devices 100A-C are implanted in bodies 105A-C respectively. The devices 100A-C are configured to communicate with sensors 1600, which are configured as a lowest level in the hierarchy of the aggregation system 1620. The aggregation system 1620 operates by receiving medical information from the devices 105A-C through the sensors 1600 to monitor the medical information of a population and may be used to determine if a local, regional or wider-scale outbreak is underway. It will be understood that the medical information can be collected anonymously so that each person's privacy can be safeguarded.

Figure 17:
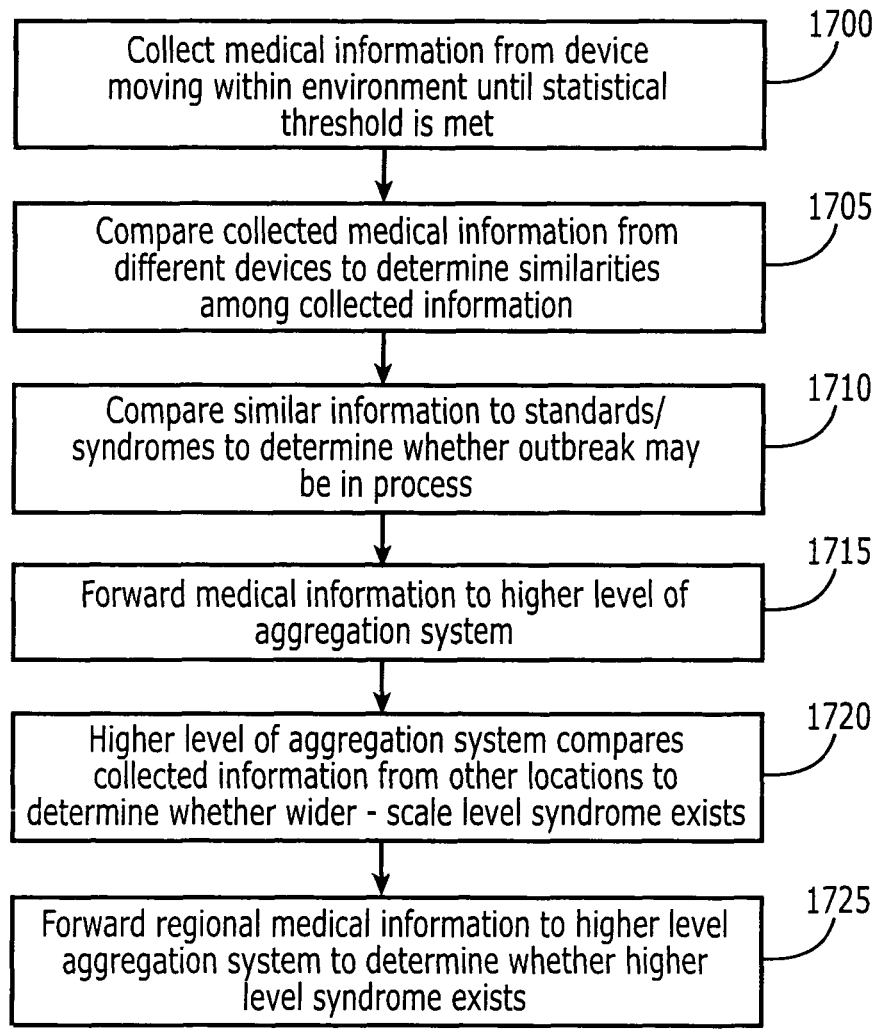
FIG. 17 is a flowchart that illustrates operations of aggregation systems in communication with mobile personal medical devices in some embodiments according to the invention.

In operation, as illustrated in FIG. 17, the medical information is collected from the devices 100A-C as the bodies 105A-C move within the environment. The aggregation system 1620 collects the medical information until a statistically significant number of samples has been acquired (block 1700).

As the medical information is continued to be collected, the aggregation system compares the collected medical information from the different devices 100A-C to determine whether there are any similarities among the information provided the devices (block 1705). Moreover, the aggregation system 1620 operates to determine whether there is a correlation between the medical information and known syndromes, such as SARS, or other diseases (block 1710). The correlation between the medical information and known syndromes can be performed, for example, as described above in reference to FIG. 6.

If a syndrome is determine to likely exist within the environment of the sampled devices 100A-C, the low level aggregation system 1620 can forward the collected medical information, and information regarding the correlation, to a higher level of the aggregation system 1620, such as system 1610 which has access to other nodes within the aggregation system 1620 that communicate with sensors that are located in different areas of the environment (block 1715). The higher levels of the aggregation system 1620 can then compare similar information and determine correlations between different regions (blocks 1705 and 1710) to determine whether a wider-scale outbreak is underway (block 1720).

In some embodiments according to the invention, the aggregation system 1620 can be scaled vertically and horizontally to cover a relatively large region, such as several different areas within a region or a number of metropolitan areas on a national or international level. It will be understood that although a nationwide aggregation system can be provided by monitoring medical information in a number of metropolitan areas, it is not necessary that all intervening areas (e.g., rural areas located between metropolitan areas) are necessarily covered by the aggregation system 1620. It will be understood that the comparisons and correlations performed at the higher levels of the aggregation system 1620 can in-turn be forwarded to still higher levels in the hierarchy of the system 1620 (block 1725).

In any event, the aggregation system 1620 at any level can take action once a syndrome has been detected including, for example, transmitting messages to the devices 100A-C whereupon the device 100A-C can transmit an alert signal so that the body 105 can be alerted to the possibility of exposure. For example, if the body 105A was exposed to and contracted SARS, the device 100A can begin measuring parameters that indicate correlation with SARS which is, in turn, communicated to the aggregation system 1620 through the sensor 1600.

Moreover, as the body 105A moves about the environment, it comes into proximity with bodies 105B and 105C. Accordingly, each of the devices 100A-C logs the proximity information indicating that each of the respective devices 100A-C was in close proximity to the others at a particular time. Later, once the aggregation system 1620 has detected the early outbreak of SARS by correlating the parameters provided by the device 100A to the parameters known to be associated with the SARS syndrome, the aggregation system can broadcast messages to the bodies 105B and C to indicate potential exposure to SARS even though each of those bodies may not yet exhibit symptoms of SARS.

The aggregation system 1620 may notify the other bodies 105B and C even though those bodies are no longer located in the same environment in which they came into close proximity with 105A initially. It will be further understood that the aggregation system 1620 may have access to the persistent storage system 1215 described above in reference to FIG. 12 so that the aggregation system can access the keys that enable the system 1620 to access the medical information in each of the devices 100A-C to further investigate the medical information associated with each of the bodies 105A-C.

In still other embodiments according to the invention, the aggregation system 1620 can broadcast a message to each or any of the bodies 105A-C to download information from the aggregation system 1620, such as a notation that the respective body was exposed to SARS at a particular time. The aggregation system 1620 may also transmit new standards and/or thresholds to the devices 100A-C that are deemed more relevant after the respective body 105A-C has been expose to a particular event. The devices 100A-C can then continue operation according to the new information downloaded from the system 1620. It will be understood that other information may be downloaded into the devices 100A-C from the system 1620.

In still further embodiments according to the invention, the aggregation system 1620 is part of a mobile wireless network, such as a cellular radio telephone network that provides service to mobile radio telephone users. In such a system, the sensor 1600 may be integrated into local radio heads or other low level pieces of infrastructure that support the wireless network. Accordingly, the messages within the aggregation system 1620 communicating the medical information may be formatted as standard messages used to transmit registration information within the network.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims are, therefore, to be read to include not only the combination of elements which are literally set forth but all equivalent elements for performing substantially the same function in substantially the same way to obtain substantially the same result. The claims are thus to be understood to include what is specifically illustrated and described above, what is conceptually equivalent, and also what incorporates the essential idea of the invention.

What is claimed:

1. A method of aggregating medical information, the method comprising:
    receiving, by a remote aggregation system including a processor, individual syndromes collected by mobile personal medical devices associated with bodies, respectively, wherein the individual syndromes comprise medical information measured within the respective bodies by the mobile personal medical devices, respectively;
    aggregating, by the remote aggregation system, the individual syndromes by comparing the individual syndromes to determine whether a similarity exists between the individual syndromes;
    receiving, by the remote aggregation system, movement information from the mobile personal medical devices;
    receiving, by the remote aggregation system, proximity information from the mobile personal medical devices, wherein the proximity information identifies groups of the mobile personal medical devices that have been in proximity to each other; and
    determining whether an environmental syndrome exists for a plurality of the individual syndromes based on the movement information, the proximity information and a determination that the similarity exists between the individual syndromes.

2. A method according to claim 1 wherein the method further comprises transmitting an alert to the plurality of mobile personal medical devices.

3. A method according to claim 1 wherein the method further comprises:
    transmitting an alert to a target mobile personal medical device that did not collect one of the individual syndromes.

4. A method according to claim 1 wherein the environmental syndrome comprises one of a plurality of hierarchically related environments, the method further comprising:
    forwarding selected ones of the individual syndromes to a higher level aggregation system responsive to determining that the selected ones of the individual syndromes match predetermined criteria.

5. A method according to claim 4 further comprising:
    transmitting a broadcast message to other mobile personal medical devices to enable transmission of the medical information to the remote aggregation system.

6. A method according to claim 5 wherein the other mobile personal medical devices are identified based on the proximity information relative to the plurality of mobile personal medical devices.

7. A method according to claim 1 wherein the receiving of the individual syndromes comprises receiving the individual syndromes with identifiers, respectively, that each identify one of the mobile personal medical devices from which the one of the individual syndromes was received, respectively, the method further comprising:
    accessing a persistent long-term storage device to retrieve historical medical information associated with one of the bodies using one of the identifiers that identifies the one of the mobile personal medical devices associated with the one of the bodies.

8. A method according to claim 7 further comprising:
    transmitting a broadcast message including respective keys obtained from the persistent long-term storage device to other mobile personal medical devices to enable transmission of the medical information from the other mobile personal medical devices to the remote aggregation system.

9. A method according to claim 1 wherein the determining of whether an environmental syndrome exists comprises:
    determining a number of the individual syndromes that match a predetermined environmental threshold, wherein the mobile personal medical devices comprise cellular telephones, and wherein the medical information measured within the respective bodies is measured by sensors implanted in the respective bodies that wireless transmit the medical information to the mobile personal medical devices.

10. A method according to claim 8 further comprising:
    transmitting an update message to the other mobile personal medical devices to record a syndrome event.

11. A method according to claim 1 further comprising:
    receiving environmental information at the remote aggregation system from a source other than by the mobile personal medical devices, wherein the medical information measured within the respective bodies is transmitted amongst the plurality of mobile personal medical devices.

12. A method according to claim 1 wherein the individual syndromes collected by the mobile personal medical devices are collected by sensors configured to communicate with the mobile personal medical devices as the devices become proximate to the sensors.

13. A system for aggregating medical information, the system comprising:
    a memory comprising computer readable program code; and
    a processor circuit coupled to the memory and configured to execute the computer readable program code to perform operations comprising:
    receiving individual syndromes collected by mobile personal medical devices associated with bodies, respectively, to aggregate the individual syndromes;
    receiving movement information from the mobile personal medical devices;
    receiving proximity information from the mobile personal medical devices, wherein the proximity information identifies groups of the mobile personal medical devices that have been in proximity to each other;
    comparing the individual syndromes to determine whether a similarity exists between the individual syndromes;
    determining whether an environmental syndrome exists for a plurality of the individual syndromes based on the movement information, the proximity information and a determination that the similarity exists between the individual syndromes, wherein the individual syndromes comprise medical information measured within the respective bodies by the mobile personal medical device devices, respectively.

14. A system according to claim 13 wherein the environmental syndrome comprises one of a plurality of hierarchically related environments, wherein the processor circuit is further configured to forward selected ones of the individual syndromes to a higher level aggregation system responsive to determining that the selected ones of the individual syndromes match at least one predetermined criteria.

15. A system according to claim 14 wherein the processor circuit is further configured to transmit a broadcast message to other mobile personal medical devices to enable transmission of the medical information to the processor circuit.

16. A system according to claim 15 wherein the other mobile personal medical devices are identified based on the proximity information relative to one of the mobile personal medical devices from which the individual syndromes have been collected.

17. A system according to claim 15 wherein the processor circuit is further configured to receive the individual syndromes with identifiers, respectively, that each identify one of the mobile personal medical devices from which the one of the individual syndromes was received, respectively, wherein the processor circuit is further configured to access a persistent long-term storage device to retrieve historical medical information associate with one of the bodies using one of the identifiers that identifies the one of the mobile personal medical devices associated with the one of the bodies.

18. A computer program product for aggregating medical information comprising:

a computer readable medium having computer readable program code embodied therein, the computer readable program product comprising:

computer readable program code configured to receive individual syndromes collected by mobile personal medical devices associated with bodies, respectively, wherein the individual syndromes comprise medical information measured within the respective bodies by the mobile personal medical devices, respectively;

computer readable program code configured to receive movement information from the mobile personal medical devices;

computer readable program code configured to receive proximity information from the mobile personal medical devices, wherein the proximity information identifies groups of the mobile personal medical devices that have been in proximity to each other;

computer readable program code configured to aggregate the individual syndromes by comparing the individual syndromes to determine whether a similarity exists between the individual syndromes; and computer readable program code configured to determine whether an environmental syndrome exists for a plurality of the individual syndromes based on the movement information, the proximity information and a determination that the similarity exists between the individual syndromes.

19. A method according to claim 1 wherein the mobile personal medical devices are implanted within the respective bodies and configured to measure parameters within the respective bodies to provide the medical information.

20. A method according to claim 1 wherein the mobile personal medical devices comprises cell phones.

* * * * *